(12) United States Patent
Kammerer et al.

(10) Patent No.: US 11,473,120 B2
(45) Date of Patent: Oct. 18, 2022

(54) REFERENCE TEST BODY, USE, TEST CHAMBER, AND METHOD

(71) Applicant: Aesculap AG, Tuttlingen (DE)

(72) Inventors: Selina Kammerer, Dauchingen (DE); Daniel Kiessling, Villingen (DE)

(73) Assignee: Aesculap AG, Tuttlingen (DE)

( * ) Notice: Subject to any disclaimer, the term of this patent is extended or adjusted under 35 U.S.C. 154(b) by 251 days.

(21) Appl. No.: 16/425,770

(22) Filed: May 29, 2019

(65) Prior Publication Data

US 2019/0376108 A1 Dec. 12, 2019

(30) Foreign Application Priority Data

Jun. 8, 2018 (DE) ...................... 10 2018 209 119.6

(51) Int. Cl.
*C12Q 1/04* (2006.01)
*C12Q 1/18* (2006.01)

(52) U.S. Cl.
CPC ............... *C12Q 1/045* (2013.01); *C12Q 1/18* (2013.01)

(58) Field of Classification Search
None
See application file for complete search history.

(56) References Cited

U.S. PATENT DOCUMENTS

| 4,271,973 A | 6/1981 | Quagliaro et al. |
| 5,523,236 A | 6/1996 | Nuzzo |
| 8,053,210 B2 * | 11/2011 | Dunkelberg .............. A61L 2/28 435/31 |

FOREIGN PATENT DOCUMENTS

DE 102 61 627.2 7/2004

OTHER PUBLICATIONS

Yale, C.E. Laboratory Animal Science. 1973, vol. 23, No. 6, pp. 885-888.*

* cited by examiner

*Primary Examiner* — Vera Afremova
(74) *Attorney, Agent, or Firm* — Lewis Kohn & Walker LLP; David M. Kohn

(57) ABSTRACT

A reference test body for monitoring and/or verifying test conditions during a test of microbial barrier properties of at least one product, wherein the reference test body has a cavity, a nutrient medium, at least one opening, and at least one cover provided with a number of holes and covering the at least one opening. A constancy of test conditions can be monitored in this way. The invention further relates to an associated use, an associated test chamber, and an associated method.

15 Claims, 3 Drawing Sheets

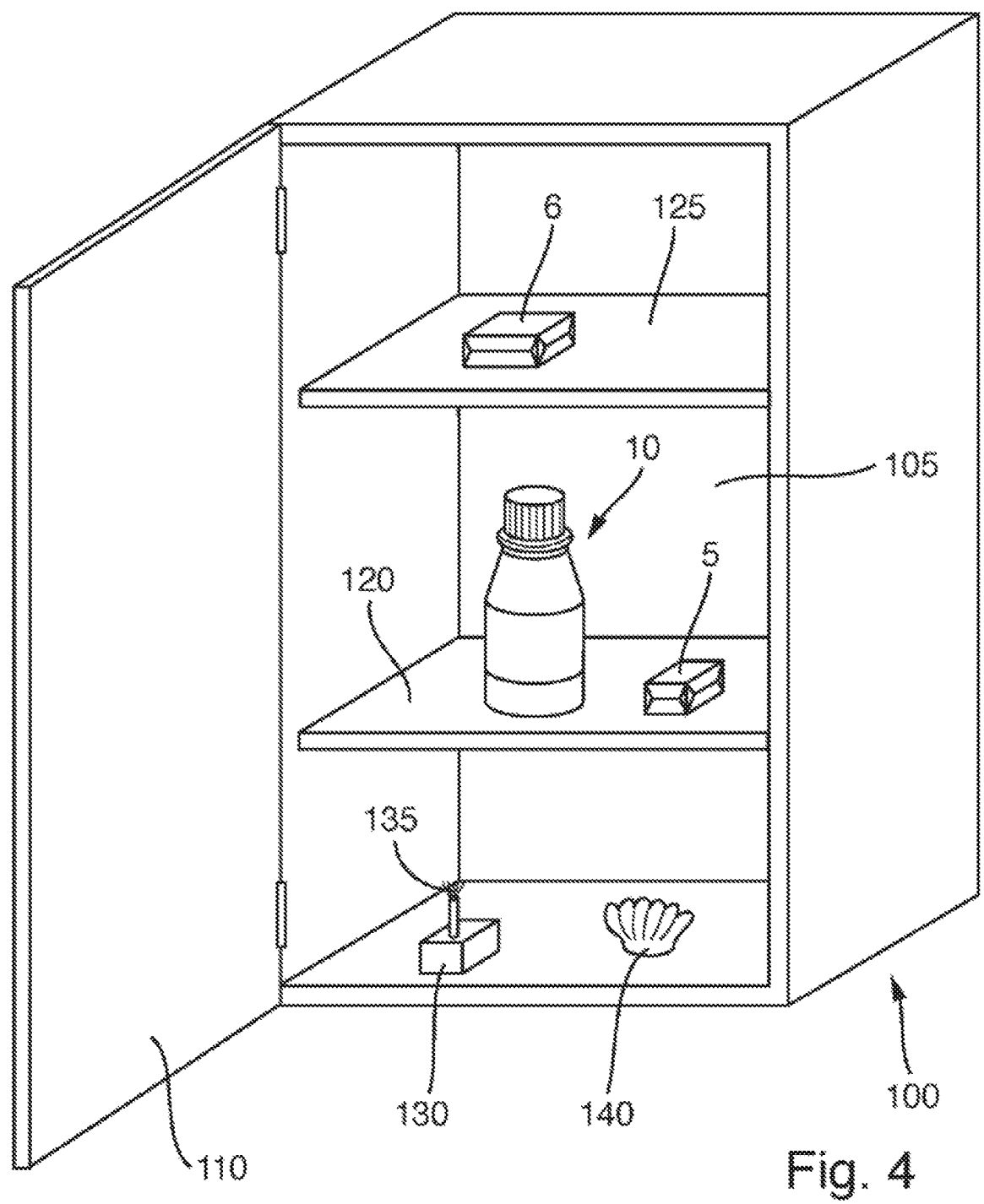

REFERENCE TEST BODY, USE, TEST CHAMBER, AND METHOD

BACKGROUND

This application is a United States Non-provisional Application claiming priority under 35 U.S.C. § 119 from German Patent Application No. DE 10 2018 209 119.6 filed Jun. 8, 2018, the entire contents of which are herein incorporated by reference.

The invention relates to a reference test body for monitoring and/or verifying test conditions during a test of microbial barrier properties of at least one product. The invention further relates to an associated use, an associated test chamber and an associated method.

Medical appliances are often sterilized at specified central locations and packed in sterile packages. Products manufactured in this way are also typically intended to maintain their sterility during subsequent transportation, for example in a hospital or by public transport. However, pressure fluctuations may occur, for example if such a product is moved in an elevator or is transported by truck.

In order to check the permanent microbial barrier properties of such products, transport operations of this kind are therefore simulated by means of test chambers. For this purpose, the products can be introduced into a test chamber, whereupon certain changeable environmental conditions are set up in the test chamber. For example, programs can be run with different pressures and temperatures. In particular, a defined quantity of microbes or germs is introduced into the test chamber, and, after completion of such a test, it is possible to determine whether germs have penetrated the respective products.

To be able to correctly assess the result of such a test, it is necessary that the same test conditions always prevail in different test runs. This could not previously be verified in a suitable way.

It is therefore an object of the invention to provide measures that permit a comparison of different test cycles.

SUMMARY OF INVENTION

According to the invention, this is achieved by a reference test body, a use of a reference test body, a test chamber and a method according to the respective main claims. Advantageous embodiments can be derived, for example, from the respective dependent claims. The content of the claims is expressly incorporated by reference into the content of the description.

The invention relates to a reference test body for monitoring and/or verifying test conditions during a test of microbial barrier properties of at least one product, in particular under pressure variations. The reference test body has a cavity. It moreover has a nutrient medium located in the cavity and provided for germs. The reference test body has at least one opening of the cavity, wherein the cavity is closed or closable except for the at least one opening. Furthermore, the reference test body has at least one cover, which closes the at least one opening and is perforated by a number of holes, i.e. is provided with a number of holes.

Within the context of the present invention, "microbes" or "germs" are to be understood as microorganisms, in particular as causative microorganisms or pathogens. For example, the expression "microbes" or "germs" is to be understood, within the context of the present invention, as bacteria and/or fungi and/or algae and/or viruses and/or subcellular structures, for example proteins and/or nucleic acids.

The expression "at least one opening", within the context of the present invention, is to be understood as one opening, i.e. a single opening, or a plurality of openings, i.e. several openings, for example two, three or four openings.

The expression "at least one cover", within the context of the present invention, is to be understood as one cover, i.e. a single cover, or a plurality of covers, i.e. several covers, for example two, three or four covers.

For example, the at least one cover can entail several covers, in particular covers stacked on top of each other and/or connected to each other, for example in the manner of a filter.

Alternatively, the at least one cover can be configured as a plurality of covers, wherein the individual covers are each arranged on different sides of the reference test body.

Within the context of the present invention, a "product" is to be understood in particular as a sterile package and/or a packaged medical product, in particular a medical product packed in a sterile package. The medical product can be a surgical instrument, for example.

The expression "sterile package", within the context of the present invention, is to be understood as a package for a medical product that is to be sterilized or that is already in a sterile state.

The expression "at least one product", within the context of the present invention, is to be understood as one product, i.e. a single product, or a plurality of products, i.e. several products, for example two, three or four products.

By means of a reference test body according to the invention, it is possible to compare several test cycles with one another, by placing such a reference test body into the corresponding test chamber and exposing it to the respective test conditions. Ideally, the same number of germs collected on the reference test body is determined at each test cycle by means of the reference test body. These germs may pass through the holes in the at least one cover. By contrast, deviations in the respective numbers of collected germs may point to different test conditions, which reduces the meaningfulness of the tests carried out.

It will be appreciated that the holes can have different shapes. For example, they can have a round, rectangular or square shape. They can also have different sizes.

Moreover, it is also possible, for example, to provide just one hole in the at least one cover that closes the at least one opening, or several holes can also be provided. The holes provided can also be so many and so small as to constitute a perforation of the at least one cover. In other words, the at least one cover can have just one hole or a plurality of holes, i.e. several holes, particularly in the form of a perforation.

The nutrient medium can be liquid, gel-like or solid. For example, the nutrient medium can be chosen from the group consisting of agar, CASO agar, CASO broth, Columbia blood agar, maximum recovery diluent and mixtures thereof. Such nutrient media have proven useful for typical cell detection procedures.

The at least one opening can be arranged in particular on a top face of the reference test body or on a side face of the reference test body. In this way, it is possible for germs to collect in a defined manner, for example germs falling by gravity from an opening arranged at the top, or germs entering through an opening arranged at the side, for example on account of a circulation of air.

The cavity can be configured such that it has no further inlet other than the at least one opening. To put it another way, the cavity can be completely enclosed except for the at least one opening and in particular also cannot be opened.

According to an alternative embodiment, the cavity has, in addition to the at least one opening, a closable inlet for the nutrient medium. This permits separate introduction of the nutrient medium, wherein the corresponding inlet can be closed after the medium has been introduced, and in this way the cavity is once again completely enclosed (except for the at least one opening).

The cavity can be completely or partially surrounded by a transparent material, in particular transparent plastic. For example, polystyrene or polyethylene terephthalate can preferably be used for this purpose. This has proven particularly useful since it permits culturing of germs in the reference test body and optical detection of resulting colonies without the germs for this purpose having to be taken out of the reference test body or without special measures having to be taken to see the cell colonies inside the reference test body.

According to a possible embodiment, the nutrient medium is arranged only at the bottom in the reference test body. This permits simple handling of the nutrient medium and simple counting of resulting cell colonies. Alternatively, however, the cavity can also be completely lined with the nutrient medium.

The at least one cover can be in particular a small stainless steel plate. The latter can have been perforated by a simple punching process for example, so that the holes can be formed.

Moreover, the at least one cover can be perforated by means of laser machining, for example.

The cavity can, for example, have the shape of a cylinder, in particular a circular cylinder, a cuboid, a cube, a sphere, a segment of a sphere or a bottle. Such shapes of the cavity have proven useful for typical applications.

The at least one opening can in particular be assigned a closure piece, by means of which the at least one opening together with the at least one cover is closable. Such a closure piece can be a plug-on or screw-on lid, for example. In this way, the at least one opening can be closed when the reference test body is not actually in a test cycle and when germs are therefore intended to be prevented from entering or leaving the reference test body. The closure piece can be configured as a separate part of the reference test body, detachable from the rest of the reference test body, or also as a separate element.

The invention further relates to a use of a reference test body for monitoring and/or verifying test conditions during a test of microbial barrier properties of at least one product. The advantages already mentioned above can be achieved in this use. As regards the reference test body, all the embodiments and variants thereof described herein can be used.

The invention further relates to a test chamber for testing microbial barrier properties of at least one product, wherein a reference test body according to the invention is arranged in the test chamber. As regards the reference test body, all the embodiments and variants thereof described herein can be used. The advantages described above can thus also be achieved. It will be appreciated that it is possible for one reference test body or several reference test bodies to be arranged in the test chamber.

The invention further relates to a method for monitoring and/or verifying test conditions during a test of microbial barrier properties of at least one product, said method having the following steps:
  introducing a reference test body according to the invention into a test chamber,
  introducing germs into the test chamber,
  generating conditions for the multiplication of germs that have penetrated the reference test body, for the purpose of culturing the germs inside or outside the reference test body,
  counting the cell colonies that have grown, and
  detecting the germs on the basis of the cell colonies that have grown.

By means of the method according to the invention, it is ensured in a particularly advantageous manner that test conditions during a test of microbial barrier properties of at least one product were set in a predetermined manner and that test conditions were constant over several test cycles. In particular, constant test conditions can be inferred from the fact that a number of grown cell colonies has a defined value or always the same value or has a value that changes only within a predetermined range.

Conditions for multiplication can be generated, for example, by the collected microorganisms and the reference test body being incubated or exposed for a certain time at a temperature of for example 35° C.-37° C. (depending on the germs or germs used). Individual germs then form cell colonies, which are optically detectable.

The method can in particular be repeated several times, in each case with the reference test bodies of the same kind. It can in this case be preferably ensured that the test conditions were the same each time the method was carried out. In the event of deviations in the number of cell colonies that have grown, this hypothesis can be disproved, i.e. it is possible to identify when the test conditions were in fact not the same. This increases the safety of the performance of the product test.

The holes formed in the at least one cover can have, for example, a diameter of 1 mm, 2 mm or different diameters between 1 mm and 2 mm. This corresponds to typical defects in the products to be tested and in their packaging, such that a comparison can be made in a realistic way. Larger or smaller dimensions of the holes are likewise possible.

Germs can be introduced into a test chamber in particular by means of an aerosol, wherein, for example, an aerosol generator can be used which discharges a germ-containing aerosol into the test chamber. In the prior art, it is known, for example, to place open Petri dishes or similar vessels into a test chamber in order to collect and detect germs for comparison purposes. However, this does not take into consideration the penetration properties of the germs. It is unable to demonstrate a constancy or reproducibility across several measurements.

A reference test body can be in the form of a container, for example, which has a perforation on at least one side. If the germs placed in the test chamber are intended to enter the reference test body solely by sedimentation, then the at least one opening is preferably situated only on a top face of the reference test body. If germs are to be detected from a laterally directed air stream, then the reference test body preferably has at least one lateral opening, i.e. a single lateral opening or several lateral openings.

Typical media for culturing germs are, as has already been mentioned, for example agar, CASO agar, CASO broth, Columbia blood agar, maximum recovery diluent or mixtures thereof. Which medium is the most preferred depends also on the germs that are to be detected. For example, an evaluation can be made, in the case of solid nutrient media, by incubation of the reference test body and, in the case of liquid nutrient media, by membrane filtration and subsequent incubation of a membrane filter on an agar plate. If a solid nutrient medium is to be used, the reference test body or a container will preferably be transparent, so that after the incubation the number of colony-forming units can be determined without great effort. A number of germs can in particular be determined by counting the germs or colonies that have grown on the nutrient medium.

A small stainless steel plate for covering the at least one opening can, for example, have a thickness of 0.1 mm. A perforation is preferably chosen such that, under typical test conditions, a still countable number of germs is collected. Countable is regarded, for example, as 300 colony-forming units per agar plate with a diameter of 90 mm.

The reference test body can be brought to a sterile state, for example before a test is carried out, by means of suitable sterilization methods, for example gas sterilization. This ensures that germs that would distort the measurement result are not present before the test.

A germ detection medium can be poured in through the at least one lateral opening already mentioned above. This is also possible in the case of a solid medium, for example agar, which can be introduced in the heated state, for example, such that it is free-flowing. The medium or the agar can also be introduced through the perforation using a syringe, in particular without a cannula, for example, provided that the perforation size allows this. The at least one lateral opening can also be used for admission of oxygen, particularly for incubation of the agar, particularly in the case of aerobic incubation. For this purpose, a lid over the inlet opening can be unscrewed slightly. Liquid media for germ capture, for example a maximum recovery diluent (peptone saline diluent), can also be added, for example via a syringe with attached cannula. This has the advantage that the reference test body is completely closed except for the perforation and germs can enter only through the perforation. The liquid germ detection medium and/or germ capture medium is removed either by aspiration through a syringe or, if appropriate, by release through the at least one lateral opening. Before it is removed, the medium ought preferably to have wetted as far as possible all sides of the reference test body, such that all germs are in fact entrained in the solution. When using liquid nutrient media, for example CASO broth, the latter can also be incubated in the reference test body and, if appropriate, the entry of germs can be inferred from any clouding that occurs.

BRIEF DESCRIPTION OF DRAWINGS

Further features and advantages will be gathered by a person skilled in the art from the exemplary embodiments described below with reference to the figures, in which:

FIG. 4 shows a test chamber.

DETAILED DESCRIPTION OF DRAWINGS

Figure 1:
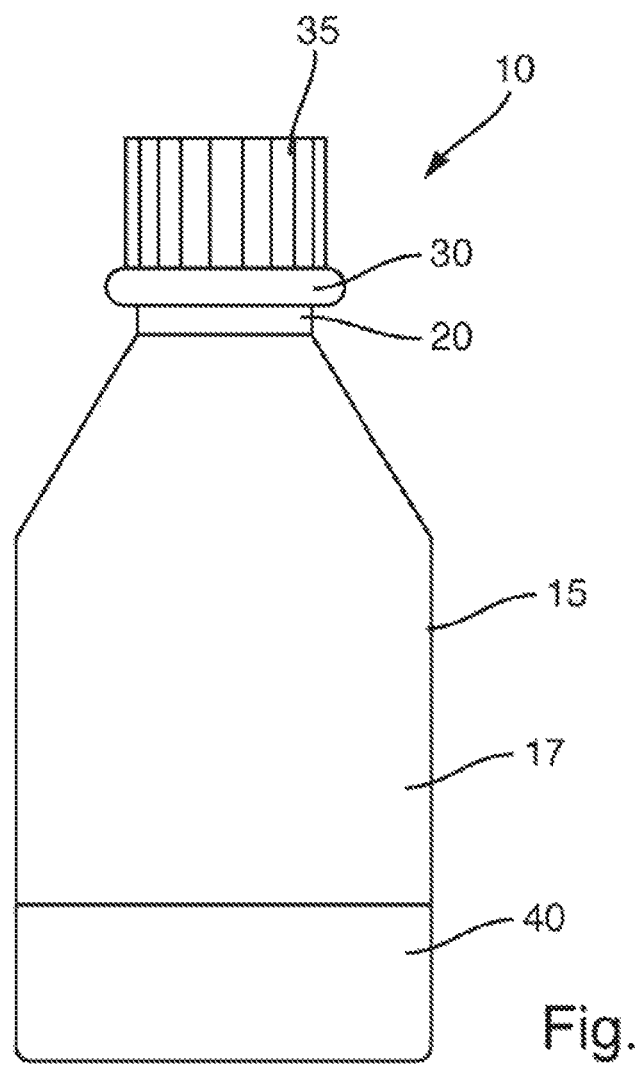
FIG. 1 shows a reference test body according to a first exemplary embodiment.

FIG. 1 shows a reference test body 10 according to a first exemplary embodiment of the invention. The reference test body 10 has a housing 15 which in the present case is made of a transparent plastic. Alternatively, the housing 15 can also be made of glass. The housing 15 has a bottle shape as shown.

At the top of the reference test body 10 there is an opening 20, which is closed by means of a cover 30. The cover 30 is perforated, as is described in more detail below with reference to FIG. 2.

The opening 20 is in the present case closed off by a lid 35, such that admission of germs into the reference test body 10 is not possible even taking into account the aforementioned perforations.

The housing 15 encloses a cavity 17 which is located inside the reference test body 10. The housing 15 and the cavity 17 are completely enclosed except for the opening 20.

A nutrient medium 40, in which germs can gather and can also possibly multiply, is arranged at the bottom of the reference test body 10.

Figure 2:
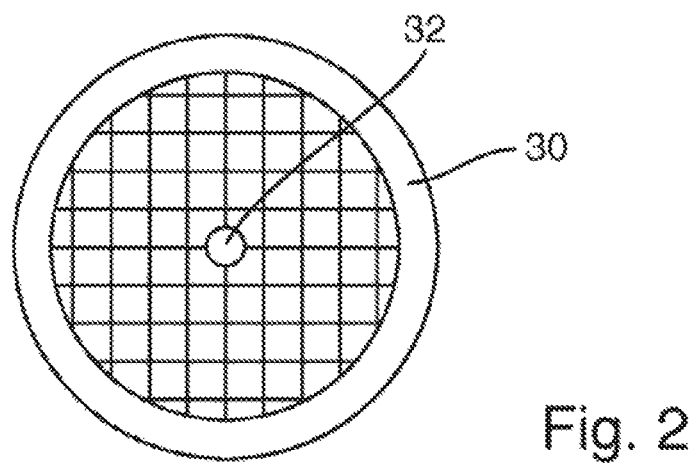
FIG. 2 shows a plan view of a cover of the reference test body.

FIG. 2 shows a plan view of the cover 30. It will be seen that the cover 30 is configured as a small plate with a hole 32 at the centre. If the lid 35 is no longer located on the reference test body 10, germs can pass through this hole 32 into the cavity 17 and can then gather in particular in the nutrient medium 40.

Figure 3:
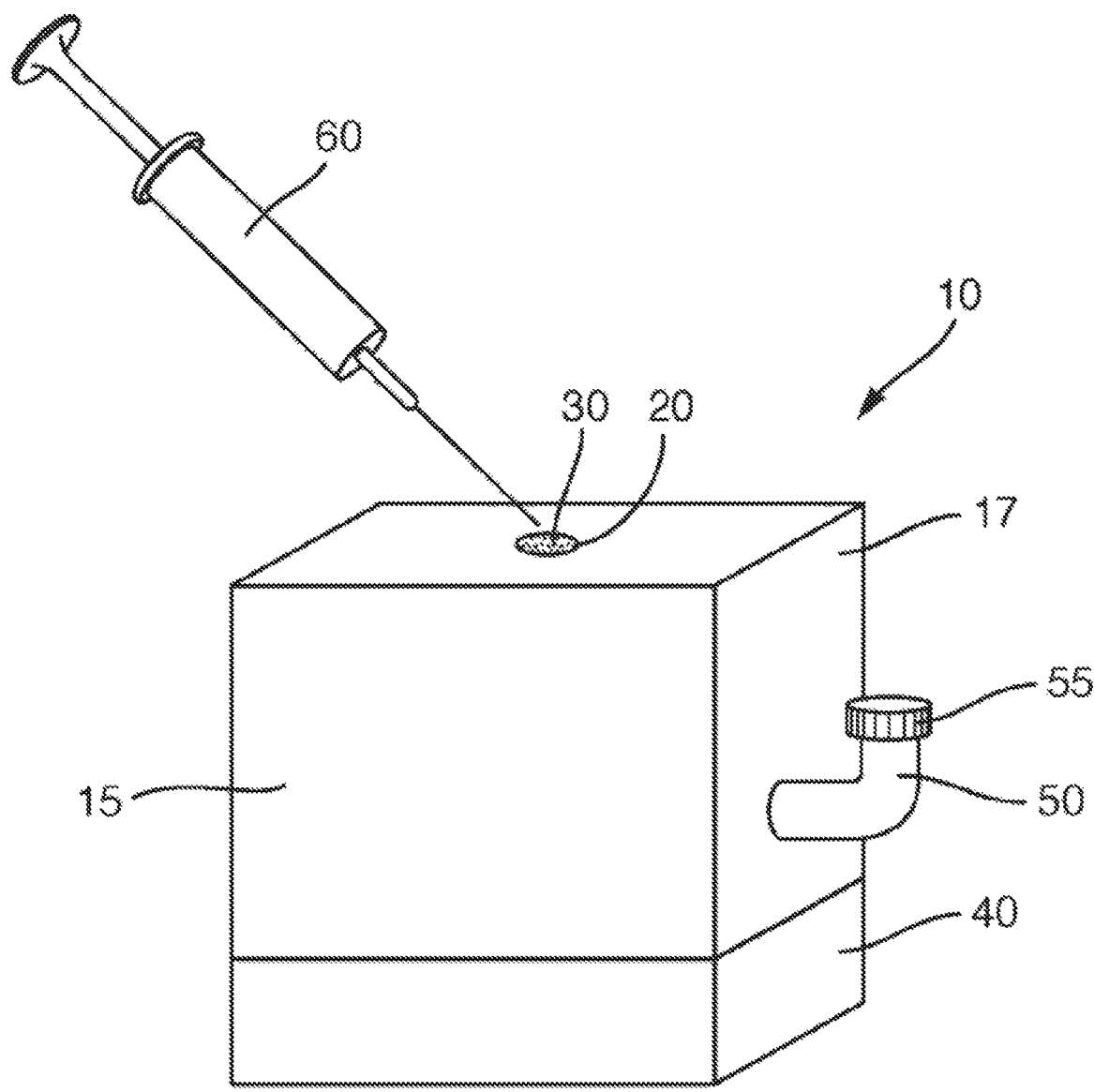
FIG. 3 shows a reference test body according to a second exemplary embodiment.

FIG. 3 shows a reference test body 10 according to a second exemplary embodiment of the invention. The housing 15 does not have a bottle shape here, but a cuboid shape. The cavity 17 is once again formed in the latter.

At the top of the reference test body 10 there is once again an opening 20, which is closed except for a perforated cover 30. As is shown, the nutrient medium 40 can be introduced through this perforation, for example by means of a syringe 60.

As an alternative to this, the nutrient medium 40 can also be introduced via a closable inlet 50 placed laterally on the reference test body 10. The closable inlet 50 is provided with a screw-on closure piece 55, such that it is tightly closable while a test is being carried out. When the screw-type closure piece 55 is removed, the nutrient medium 40 can be topped up, particularly if it is liquid or can be made liquid by heating.

FIG. 3 shows two different possibilities for introducing nutrient medium.

FIG. 4 shows a test chamber 100 according to an exemplary embodiment of the invention.

The test chamber 100 has a test space 105, which is provided for testing products 5, 6. The products 5, 6 are shown here schematically and only by way of example, wherein they can in particular be products provided with a microbe-proof or germ-proof packaging that is intended to be tested.

In the present example, two insert shelves 120, 125, on which the products 5, 6 are mounted, are arranged in the test space 105.

Alongside the product 5, a reference test body 10 is also arranged on the lower insert shelf 120.

The test chamber 100 is closable by means of a closing element in the form of a door 110. When the door 110 closes the test space 105, the latter is sealed off in a pressure-tight manner, such that different pressures can be simulated.

This purpose is served by a bellows 140 which is arranged in the test space 105 and which can be inflated and also reduced in size again from the outside, such that an air pressure inside the test space 105 can change. In this way, different pressures can be set, and, for example, a typical transport operation can thus be simulated. No air exchange with the test space 105 takes place here, such that no germs can escape, and no concentration of germs is changed.

The test space 105 also accommodates an aerosol generator 130, which sprays an aerosol 135 into the test space 105. This aerosol 135 contains germs, and the products 5, 6 are typically intended to be tested for impermeability to penetration of these germs.

The reference test body 10 shown in FIG. 4 is still closed by means of a lid 35. The lid 35 is taken off before the products 5, 6 are tested for impermeability to germs or microbial barrier properties, such that germs distributed in the test space 105 can pass through the hole 32 into the cavity 17. After the test, the germs that have collected in the nutrient medium 40 are cultured by placing the reference test body 10 in suitable culture conditions, in particular by incubation of the reference test body 10 at a temperature of, for example, 35° C.-37° C. (depending on the respective germ or respective germs used). Individual cells form cell colonies, which are optically detectable and countable.

Tests of this kind are preferably carried out several times in succession. This can be done using different products 5, 6. If the number of germs collected and counted in the reference test body 10 is then always the same or similar, it can be inferred from this that the test conditions are at least approximately the same. However, if the number of germs collected changes considerably, this indicates that the test conditions were not constant. By such verifying, the meaningfulness of the tests carried out on the products 5, 6 can thus be considerably improved.

The invention claimed is:

1. A method for monitoring and/or verifying test conditions for increasing safety of performing product testing during a test of microbial barrier properties of at least one product, said method having the following steps:
    (a) introducing the at least one product and a reference test body for monitoring and/or verifying the test conditions during the test of microbial barrier properties of the at least one product into a test chamber,
    (b) introducing germs into the test chamber,
    (c) generating conditions for the multiplication of germs that have penetrated the reference test body, for the purpose of culturing the germs inside or outside the reference test body,
    (d) counting the cell colonies that have grown, and
    (e) detecting the germs on the basis of the cell colonies that have grown, wherein the reference test body comprises a cavity, a nutrient medium located in the cavity and provided for germs, at least one opening of the cavity, wherein the cavity is closed or closable except for the at least one opening, and at least one cover, which closes the at least one opening and is perforated by a number of holes, wherein the method is repeated several times, wherein constant test conditions are inferred from a number of grown cell colonies having a defined value or always the same value, and wherein deviations in a number of grown cell colonies point to different test conditions.

2. The method of claim 1, wherein the nutrient medium is liquid or solid.

3. The method of claim 1, wherein the at least one opening is arranged on a top face of the reference test body or on a side face of the reference test body.

4. The method of claim 1, wherein the cavity has no further inlet other than the at least one opening.

5. The method of claim 1, wherein the cavity has, in addition to the at least one opening, a closable inlet for the nutrient medium.

6. The method of claim 1, wherein the cavity is completely or partially surrounded by a transparent material.

7. The method of claim 1, wherein the nutrient medium is arranged only at the bottom in the reference test body.

8. The method of claim 1, wherein the cavity is lined completely with the nutrient medium.

9. The method of claim 1, wherein the at least one cover is a small stainless steel plate.

10. The method of claim 1, wherein the at least one cover is perforated by means of laser machining.

11. The method of claim 1, wherein the cavity has the shape of a cylinder, in particular a circular cylinder, a cuboid, a cube, a sphere, a segment of a sphere or a bottle.

12. The method of claim 1, wherein the at least one opening is assigned a closure piece, by means of which the at least one opening together with the at least one cover is closable.

13. The method of claim 6, wherein the transparent material is a transparent plastic.

14. The method of claim 13, wherein the transparent plastic is polystyrene or polyethylene terephthalate.

15. A method for monitoring and/or verifying test conditions for increasing safety of performing product testing during a test of microbial barrier properties of at least one product, said method having the following steps:
    (a) introducing the at least one product and a reference test body for monitoring and/or verifying the test conditions during the test of microbial barrier properties of the at least one product into a test chamber,
    (b) introducing germs into the test chamber,
    (c) generating conditions for the multiplication of germs that have penetrated the reference test body, for the purpose of culturing the germs inside or outside the reference test body,
    (d) counting the cell colonies that have grown, and
    (e) detecting the germs on the basis of the cell colonies that have grown, wherein the reference test body comprises a cavity, a nutrient medium located in the cavity and provided for germs, at least one opening of the cavity, wherein the cavity is closed or closable except for the at least one opening, and at least one cover, which closes the at least one opening and is perforated by a number of holes, wherein the method is repeated several times, wherein constant test conditions are inferred from a number of grown cell colonies having a value that changes only within a predetermined range, and wherein deviations beyond said predetermined range in a number of grown cell colonies point to different test conditions.

* * * * *